US012616658B2

(12) United States Patent
Balu-Iyer et al.

(10) Patent No.: US 12,616,658 B2
(45) Date of Patent: May 5, 2026

(54) METHOD FOR PREPARATION OF LIPOSOMES

(71) Applicant: The Research Foundation for The State University of New York, Amherst, NY (US)

(72) Inventors: Sathy V. Balu-Iyer, Amherst, NY (US); Nhan Hanh Nguyen, Amherst, NY (US); Dominique Weeks, Amherst, NY (US); Vincent Chak, Amherst, NY (US); Milagros Riquelme Gonzalez, Amherst, NY (US)

(73) Assignee: The Research Foundation for the State University of New York, Amherst, NY (US)

( * ) Notice: Subject to any disclaimer, the term of this patent is extended or adjusted under 35 U.S.C. 154(b) by 451 days.

(21) Appl. No.: 18/003,904

(22) PCT Filed: Jul. 1, 2021

(86) PCT No.: PCT/US2021/040103
§ 371 (c)(1),
(2) Date: Dec. 29, 2022

(87) PCT Pub. No.: WO2022/006406
PCT Pub. Date: Jan. 6, 2022

(65) Prior Publication Data
US 2023/0255888 A1    Aug. 17, 2023

Related U.S. Application Data

(60) Provisional application No. 63/047,068, filed on Jul. 1, 2020.

(51) Int. Cl.
*A61K 9/1278*    (2025.01)
*A61K 45/06*    (2006.01)

(52) U.S. Cl.
CPC ............ *A61K 9/1278* (2013.01); *A61K 45/06* (2013.01)

(58) Field of Classification Search
CPC ...... A61K 9/1278; A61K 45/06; A61K 38/00; A61K 9/1277; A61K 9/127
See application file for complete search history.

(56) References Cited

U.S. PATENT DOCUMENTS

| | | | |
|---|---|---|---|
| 2006/0078605 A1 | 4/2006 | Mammarella | |
| 2007/0059318 A1 | 3/2007 | Balu-Iyer et al. | |
| 2014/0302014 A1 | 10/2014 | Narain et al. | |
| 2017/0105936 A1 | 4/2017 | Cerundolo et al. | |
| 2017/0209371 A1* | 7/2017 | Balu-Iyer ........... | A61K 38/1709 |
| 2019/0151426 A1 | 5/2019 | Balu-Iyer et al. | |

FOREIGN PATENT DOCUMENTS

| | | |
|---|---|---|
| CN | 101304757 A | 11/2008 |
| JP | H05000239 A | 1/1993 |
| JP | 2008127327 A | 6/2008 |
| JP | 2009532371 A | 9/2009 |
| JP | 2020510705 A | 4/2020 |

OTHER PUBLICATIONS

Glassman et al. (Subcutaneous Administration of Lyso-Phosphatidylserine Nanoparticles Induces Immunological Tolerance Towards Factor VIII in a Hemophilia A Mouse Model, Int J Pharm, Sep. 5, 2018). (Year: 2018).*

Dwivedi et al., "Review on Preparation and Characterization of Liposomes with Application," Journal of Scientific & Innovative Research, Mar.-Apr. 2013, pp. 486-508, vol. 2, Issue 2.

Bowen, "Particle Size Distribution Measurement from Millimeters to Nanometers and from Rods to Platelets," Journal of Dispersion Science and Technology, 2002, pp. 631-662, vol. 23, No. 5.

Glassman, F.Y., et al., Subcutaneous Administration of Lyso-Phosphatidylserine Nanoparticles Induces Immunological Tolerance Towards Factor VIII in a Hemophilia A Mouse Model, Sep. 5, 2018, Int. J. Pharm., vol. 548, No. 1, pp. 642-648.

* cited by examiner

*Primary Examiner* — Robert A Wax
*Assistant Examiner* — John Seungjai Kwon
(74) *Attorney, Agent, or Firm* — Hodgson Russ LLP

(57) ABSTRACT

Disclosed are methods of preparing liposomes without size exclusion steps resulting in small sized liposomes exhibiting narrow size distribution and compositions of same. The methods utilize liposome formation from lyso-PS, PS, and PC as the only phospholipids.

15 Claims, 2 Drawing Sheets

METHOD FOR PREPARATION OF LIPOSOMES

CROSS-REFERENCE TO RELATED APPLICATIONS

This application claims priority to U.S. provisional patent application No. 63/047,068, filed on Jul. 1, 2020, the disclosure of which is incorporated herein by reference.

STATEMENT REGARDING FEDERALLY SPONSORED RESEARCH

This invention was made with government support under contract no. HL070227 awarded by the National Institutes of Health. The government has certain rights in the invention.

BACKGROUND OF THE DISCLOSURE

A liposome is a closed structure made of a lipid bilayer. The bilayer encloses an aqueous phase (inner water phase). Current methods of preparation of liposomes generally start with an emulsification step where an oil phase containing lipids dissolved in an organic solvent is mixed with a water phase and stirred. The organic solvent is then evaporated leaving an aqueous solution containing liposomes. The liposomes prepared by such a process, however, are a heterogeneous size population, and generally large (1 micron and above). To reduce the size where smaller liposomes are desired, filtration or extrusion steps are carried out. However, filtration and extrusion can cause lipid loss affecting the loading efficiency of the liposomes. Moreover, the extrusion step poses challenges during manufacturing process and scaling up is not easily achieved.

SUMMARY OF THE DISCLOSURE

The present disclosure provides compositions and methods for preparing liposomes without size exclusion steps, but nevertheless generating small-sized liposomes exhibiting narrow size distribution that is comparable to methods using size exclusion steps. The elimination of size exclusion steps is achieved by using lyso-PS. Avoiding a size-exclusion step results in reduced lipid loss and is advantageous for the manufacturing process.

BRIEF DESCRIPTION OF THE FIGURES AND TABLES

DETAILED DESCRIPTION OF THE DISCLOSURE

Figure 1:
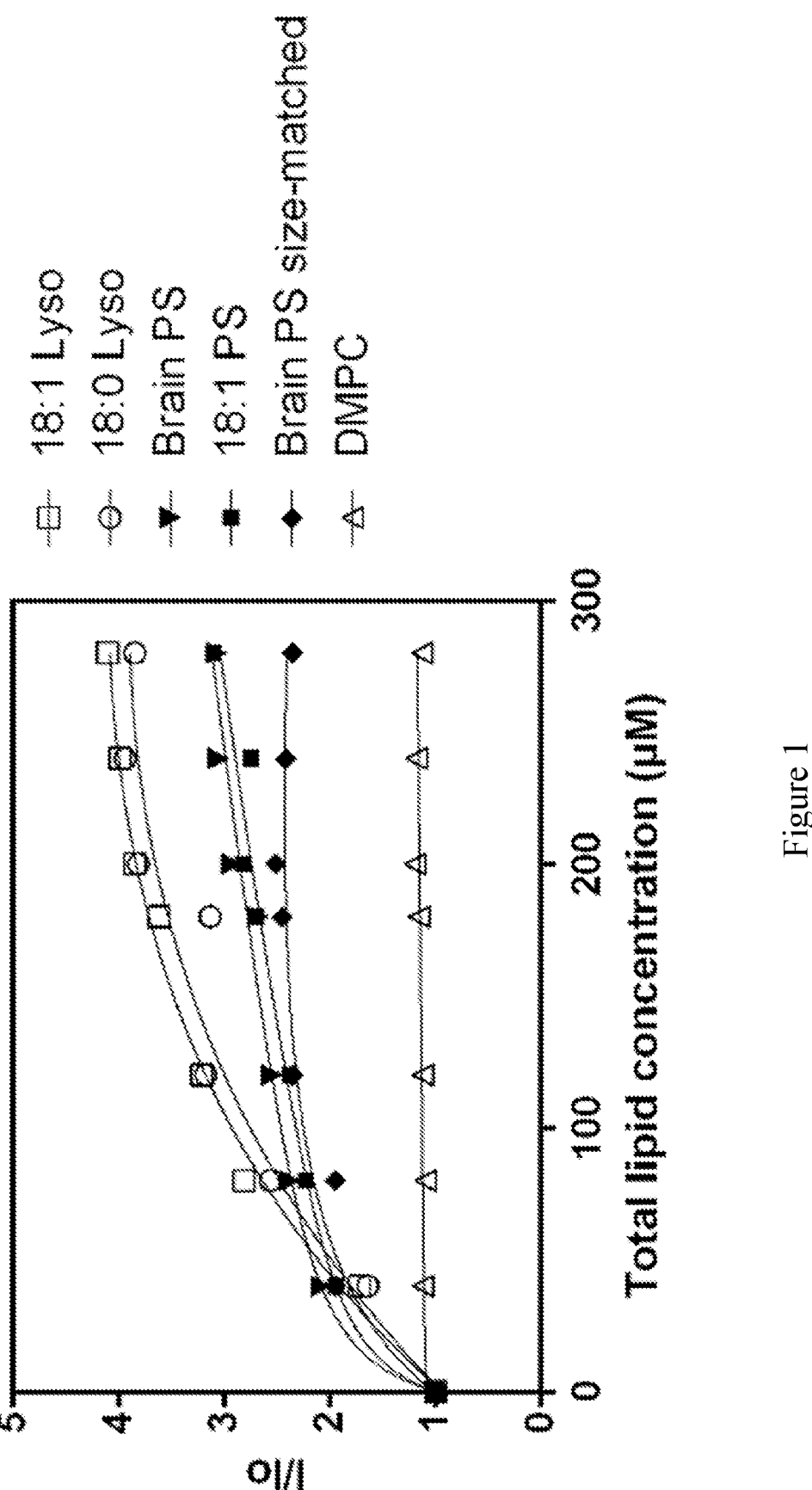
FIG. 1 shows exposure of PS as a function of lipid concentration.
Figure 2:
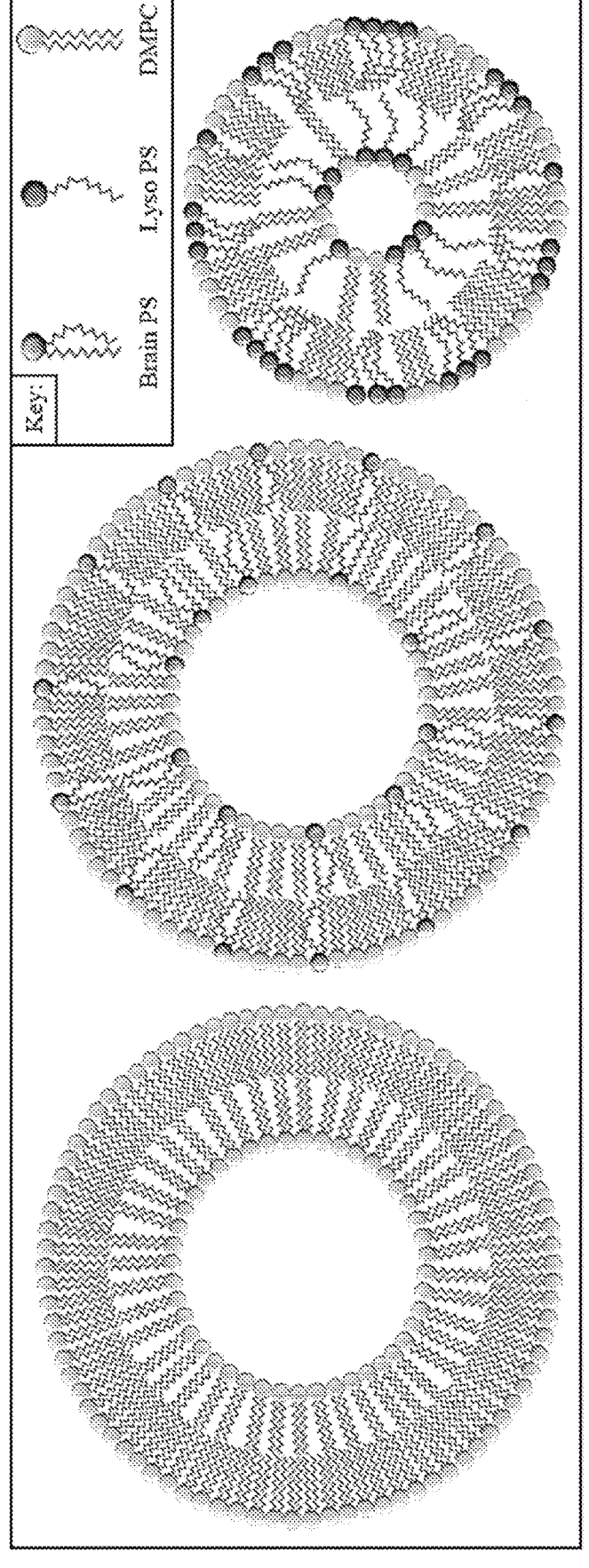
FIG. 2 shows a schematic representation of liposomes composed of PC alone, PC containing double chain PS and PC containing lyso-PS.

The present disclosure provides methods for preparing liposomal compositions that are suitable for delivery of protein/peptides such that induction of immune tolerance is achieved. The method of preparation of liposomes uses materials such that no size exclusion step is required during the entire process and yet small-sized, uniform distribution liposome population can be obtained. Elimination of a size exclusion step is advantageous in the manufacturing process for preparation of liposomal compositions.

Throughout this application, the use of the singular form encompasses the plural form and vice versa. For example, "a", or "an" also includes a plurality of the referenced items, unless otherwise indicated.

Every numerical range given throughout this specification includes its upper and lower values, as well as every narrower numerical range that falls within it, as if such narrower numerical ranges were all expressly written herein.

By "lipidic structures" is meant liposomes and other structures such as, for example, micellar structures, liposomes, cochleates, molecular assemblies, and the like.

The term "lyso" when used herein in conjunction with a phospholipid means that the glycerol part of the molecule has only one acyl chain instead of two. For example, lyso-PS has only one acyl chain whereas PS has two acyl chains.

"Liposomes" may be referred to herein as lipidic nanoparticles, or nanoparticles. The liposomes may comprise PC and PS, where some or all PS is in the form of lyso-PS. The liposomes may contain PS, lyso-PS, and PC as the only phospholipids. The liposomes may contain lyso-PS and PC as the only phospholipids. The PS or lyso-PS may be in a range of from 10% to 30% of the total phospholipids in the bilayer with the remaining phospholipids being mainly PC or only PC. For example, the lyso-PS can be from 10 to 50%, or 15 to 50%, or 15 to 30%, with the remaining phospholipids being PC. The liposomes may have a ratio of PC:lyso-PS as 90:10, 80:20, 70:30, 60:40, or 50:50 molar ratios. Only the PS (some or all) is in the form of lyso-PS, while all of PC has two acyl chains. In an embodiment, phosphatidylethanolamine (PE) may be added. PE may be added at the expense of PC up to 20 mol %. In various examples, the liposomes do not contain any PG. The phospholipids for preparing the liposomes can be obtained from any available source such as plant or animal. The phospholipids are commercially available or can be synthesized by known methods. For example, PS can be obtained from porcine brain PS or plant-based soy (e.g., soya bean) PS. Lyso-PS is also available commercially.

PC may have from 14 to 20 carbons (and all integer number of carbons and ranges therebetween (e.g., 14, 15, 16, 17, 18, 19, or 20)). In various examples, the PC is not be lyso-PC.

The acyl chain for lyso-PS may have from 16 to 20 carbons (e.g., 16, 17, 18, 19, or 20). It should have at least one double bond. For example, it can be 18:1. It may have 2 or 3 double bonds. Without intending to be bound by any particular theory, it is considered that the stability of the liposomes may be the better with a single double bond than with 2 or 3 double bonds. However, at least one double bond was found to be necessary for enhanced effectiveness. The chain length of PC and lyso-PS may be same or different.

In an embodiment, the PC:PS ratio is 90:10 to 60:40, including all ratio values and ranges therebetween, and all of the PS is lyso-PS. In an example, the PC:lyso-PS may be 85:15 to 65:35, including all ratio values and ranges therebetween. In an example, the ratio of PC:lyso-PS may be 70:30 (molar ratio). In an example, the lyso-PS is from 15 to 50% (including all ratio values and ranges therebetween) or 15 to 35% (including all ratio values and ranges therebetween) with the remaining phospholipids being PC. The lyso-PS and PC may be the only phospholipids present in the bilayer of the liposomes. In an embodiment, the lyso-PS can be up to 90% of the total phospholipids of the liposome, with the remaining being PC. In various other embodiments, some of the PC may be replaced with PE.

The use of lyso-PS in the preparation of liposomes surprisingly resulted in small-sized and uniform sized population of liposomes even without a size exclusion step, such as extrusion. The method for preparation of liposomes without using a size-exclusion step is as follows. The process involves thin lipid film hydration using desired molar ratios of phospholipids, such as lyso-PS and PC. The lipids may be dissolved in an organic solvent, such as, for example, chloroform or ethanol or methanol or isopropyl ether and the solvent is allowed to dry. The lyso-PS, PC film is then rehydrated in an appropriate buffer such as (Tris, Citrate, PBS or the like). The preceding steps may be carried out at room temperature. The composition may then be incubated at a temperature higher than room temperature, such as 37° C., for a short period of time (such as from 30 seconds to 5 minutes) followed by vortexing (from about 30 seconds to 3 mins). The process can be repeated. For example, the process can be repeated 2 to 5 times. Vortexing may be replaced by equivalent mixing alternatives, such as, for example, gentle mixing, swirling, shaking, or the like, or combinations thereof.

The lipidic particles do not need to be extruded or subjected to any other size-exclusion process (e.g., density gradient, sonication, etc.) and are preferably not subjected to extrusion or another size-exclusion step. Rather, the lipidic particles can directly be used for association/loading with protein. In an embodiment, protein may be loaded by a trigger-loading process, whereby temperature is increased to change the conformation of the protein. The altered conformation protein is then incorporated into the liposomes and once cooled down to room temperature reverts to its original conformation, but now is incorporated into the liposomal bilayer.

In an embodiment, the liposomes may also comprise immune modulating agents, such as rapamycin and/or retinoic acid. The addition of the immune modulating agents could be carried out either before drying the solvent or to dry lipid film as solution and alternatively after liposome formation.

The loading of protein on to liposomes or into the bilayer of the liposome can be carried out by trigger loading technique. As a first step, conformationally altered state is generated by an increase in temperature and/or a decrease in pH. Protein can be loaded on to the liposomes by exposing protein to an elevated temperature which will result in unfolding of the protein (such as up to 70° C.). Different protein may require different temperatures that can be determined by controlled folding studies where native conformation of the protein is recoverable after removal of stress. This is described in U.S. Pat. No. 7,625,584, the relevant portions of which are incorporated herein by reference. The temperature also may be determined by acyl chain length of PC lipid. Without intending to be bound by any particular theory, it is considered that the longer the chain length higher the temperature. For example, for a 14 carbon chain length, a temperature of 15-25° C. may be used. In another example, for a 16 carbon chain length, a temperature of 40-50° C. may be used. In another example, for a 18 carbon chain length, a temperature of 50-60° C. may be used. In embodiments, protein may be heated up to from 50 to 69° C., such as up to 50, 51, 52, 53, 54, 55, 56, 57, 68, 59, 60, 61, 62 63, 64, 65, 66, 67, 68, or 69° C. When incubated with the lyso-PS liposomes in this state, the protein is able to intercalate into the liposomal bilayer. In various examples, the protein can intercalate into the liposome at various pH's and temperatures. For example, the pH may be 2-8, including all 0.1 pH values and ranges therebetween. For example, the pH may be 2, 2.5, 3, 3.5, 4, 4.5, 5, 5.5, 6, 6.5, 7, 7.4, 7.5, or 8. The temperature during intercalation may be room temperature or higher (e.g., room temperature –70° C., including all 0.1° C. values and ranges therebetween (e.g., 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70° C.). For example, the pH may be acidic (e.g., 2-6, 2, 2.5, 3, 3.5, 4, 4.5, 5, 5.5, 6) and the temperature may be room temperature or 37° C. The liposomes can then be cooled down to room temperature (generally between 18 to 25° C., such as, for example, 18, 19, 20, 21, 22, 23, 24 or 25° C.). The pH range can be from 3 to 8, including all 0.1 pH values and ranges therebetween (e.g., 3, 4, 5, 6, 7, or 8). The present liposome compositions can be stored at room temperature in a freeze dried state for several months or in liquid or reconstituted state for up to 48 hours, in the freezer for months, and refrigerated conditions in solid state for months and in liquid state for weeks.

A protein may be associated with liposomes in different configurations. For example, protein may be intercalated (e.g., intercalated into the bilayer), on the surface of the liposome, or encapsulated (e.g., encapsulated in the interior of the liposome). Using the trigger loading method generally leads to incorporation into the bilayer.

Various proteins may be associated with the liposomes. Non-limiting examples of proteins that may be associated with a liposome of the present disclosure include AAV proteins (e.g., AAV 8), collagens, aquaporin 4, cas proteins (e.g., cas9), insulin, Factor VIII, Adalimumab, alpha glucosidase (GAA), and the like.

It was observed that the present method resulted in the generation of small liposomes of uniform size. It was surprising that small sized liposomes exhibiting a narrow size distribution would be obtained without the need for extrusion or other size exclusion steps. In embodiments, the mean size (e.g., average diameter) of liposomes prepared may be 50 to 400 nm, including all nm values and ranges therebetween, with at least 80% of the liposomes having a diameter from 50 to 400 nm. In an embodiment, the mean size (e.g., average diameter) of liposomes prepared may be 200 to 300 nm, including all nm values and ranges therebetween. In an embodiment, the liposomes prepared may have an average size (e.g., average diameter) of 200 to 300 nm, including all nm values and ranges therebetween, with at least 80% of the liposomes having a diameter from 200 to 300 nm, including all nm values and ranges therebetween. In embodiments, at least 85, 90, 95, 96, 97, 98, or 99% of the liposomes may have a diameter of from 200 to 300 nm, including all nm values and ranges therebetween.

In an embodiment, the liposomes prepared have an average size (e.g., average diameter) less than 300 nm (such as, for example, 200-300 nm) with at least 90-95% (e.g., 90%, 91%, 92%, 93%, 94%, or 95%) of the particles being (e.g., having a diameter) 200-275 nm, including all nm values and ranges therebetween.

The zeta potential of the liposomes prepared by the present method is about 25. In embodiments, it may be from about 10 to about 40, (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40).

Lipid loss in the present method is significantly less than a method that includes a size exclusion step, such as extrusion. The lipid recovery after each step can be determined using a standard phosphate assay. Lipid recovery using the present method was observed to be over 98%, meaning there is less than 2% loss. In various embodiments, the lipid loss may be less than 5%, less than 4%, less than 3%, less than 2%, or less than 1%. In contrast, lipid loss in methods employing extrusion steps is typically about 10%.

In an embodiment, this disclosure provides a method of preparing liposomes of less than average 300 nm size (e.g., an average diameter), with at least 95% of the particles being 200-275 nm (e.g., in diameter) comprising mixing lipids comprising lyso-PS, and vortexing, where the liposomes formed have an average size (e.g., average diameter) of less than 300 nm and 95% of the particles have a size (e.g., diameter) of 200 to 275 nm. Proteins may be trigger loading a protein into the liposomal bilayer. In an embodiment, the lyso-PS is 16:1 or 18:1 or a combination thereof. In an embodiment, the lyso-PS is L-lyso-PS only, D-lyso-PS only, or a combination.

The present method results in high loading efficiency. Protein can be loaded on to the lyso-PS-liposomes at molar ratios from 1:100 to 1:10,000 (and all ratios therebetween). In embodiments, the ratio may be 1:500, 1:1,000, 1:2,500, 1:5,000, 1:7,500 or 1:10,000, and all ratios and ranges between these ratios.

The present liposomes can be used for preparation of pharmaceutical compositions for administration to an individuals. For example, the present liposomes may be formulated in a suitable carrier. A suitable carrier may be a buffer or other pharmaceutical carriers or additives, excipients, stabilizers, or a combination thereof. For example, the liposomes may be formulated in sugars, starches, cetyl alcohol, cellulose, powdered tragacanth, malt, gelatin, talc, oils, glycols, glycerol monooleate, polyols, polyethylene glycol, polymers such as chitosan, enteric coating, ethyl alcohol, additional emulsifiers and the like. Examples of pharmaceutically acceptable carriers, excipients, and stabilizers can be found in *Remington: The Science and Practice of Pharmacy* (2020) 23rd Edition, Philadelphia, PA Elsevier Science.

Liposomes prepared by the present methods can be formulated for delivery via any route. For example, the present liposomes may be formulated for oral delivery. The composition may be directly delivered to the desired location in the gastrointestinal tract using gavage. Alternatively, the liposomes may be formulated in the form of liquid, suspensions, tablets (including enteric coated tablets), gels, capsules, powder or any other form that can be ingested. Formulations can include pharmaceutical carriers known to be used for oral formulations. The formulations can be pediatric formulations, which can include various flavors and the like. The compositions may alternatively be delivered by any standard route such as intravenous, intramuscular, intraperitoneal, mucosal, subcutaneous, transdermal, intradermal, oral, and the like.

The present compositions may be administered to subject, which may be a mammal. The mammal can be a human, domesticated animals or pets, farm animals, non-human primates and the like. Examples include dog, cat, horse, or cow, but are not limited to these examples. A subject can be male or female.

The following Examples provide various embodiments of the present disclosure.

Example A. A method of preparing liposomes having an average diameter of less than 300 nm, wherein at least 95% of the particles have a diameter of 200-275 nm, comprising: mixing a plurality of lipids comprising phosphatidylcholine (PC) and lysophosphatidylserine (lyso-PS), wherein the ratio of PC to lyso-PS is from 90:10 to 60:40, and vortexing the mixture, wherein the liposomes formed have an average diameter of less than 300 nm and 95% of the particles have a diameter of 200-275 nm, wherein the method does not comprise a size exclusion step.

Example B. A method according to Example A, wherein the size exclusion step is an extrusion step.

Example C. A method according to Example A or Example B, wherein the ratio of PC to lyso-PS is from 85:15 to 70:30.

Example D. A method according to any one of Examples A-C, wherein the PC is present as dimyristoyl-sn-glycero-3 phosphatidylcholine (DMPC).

Example E. A method according to any one of Examples A-D, wherein PC and lyso-PS are the only phospholipids present in the bilayer of the liposomes.

Example F. A method according to any one of Examples A-E, wherein the lyso-PS is 18:1.

Example G. A method according to any one of Examples A-F, wherein the lyso-PS is L-lyso-PS.

Example H. A method according to any one of Examples A-G, wherein the vortexing is done from 30 seconds to 3 minutes.

Example I. A method according to any one of Examples A-H, further comprising trigger loading a protein into the liposome.

Example J. A method according to Example I, wherein the protein is loaded into a liposomal bilayer.

Example K. A method according to Example I or Example J, wherein the conformation of the protein is altered by heating the protein to about 37° C.

Example L. A method according to any one of Examples I-K, wherein the protein is chosen from AAV proteins (e.g., AAV 8), collagens, aquaporin 4, cas proteins (e.g., cas9), insulin, Factor VIII, Adalimumab, and alpha glucosidase (GAA).

The following examples are provided for illustrative purposes and are not intended to be limiting.

Example 1

This example describes preparation of liposomes using the present method and also describes characteristics of the liposomes prepared by this method.

Biophysical Characterizations of Non-Extruded Liposomes.

Method: Lyso-PS film was rehydrated in appropriate buffer (Tris, pH 7.08; Citrate, pH 5.0; or PBS, pH 7.4), then incubated at 37° C. for 2 min followed by 15 sec vortexing. This process was repeated for a total of 3 cycles. Association of the nanoparticles with FVIII, insulin, and Adalimumab was conducted through the trigger-loading method at 37° C., 63° C., or 55° C., respectively for 30 min.

Results:

TABLE 1

| | Extruded Lyso-PS nanoparticles | | | |
| --- | --- | --- | --- | --- |
| | Unloaded Lyso-PS nanoparticles | FVIII-associated Lyso-PS nanoparticles | Insulin-associated Lyso-PS nanoparticles | Adalimumab-associated Lyso-PS nanoparticles |
| Size (nm) | 111.7 ± 9.61 | 194.8 ± 7.9 | 93.6 ± 20.24 | 118.9 |
| Polydispersity index | 0.17 ± 0.05 | 0.21 ± 0.02 | 0.32 ± 0.06 | 0.63 |
| Zeta potential (mV) | −24.98 ± 3.7 | −15.0 ± 1.9 | −24.9 ± 0.4 | |
| Association efficiency (%) | — | 43.8% ± 7.4 | 84.8% ± 16.3 | 87.9% ± 8.6 |

Associated efficiency was calculated based on the theoretical amount of loaded protein. Percentage of FVIII recovery is approximately 40-50%. Associated efficiency for adalimumab was calculated based on the formulation (Top+Middle)/(Top+Middle+Bottom). Percentage of Adalimumab recovery is approximately 50-60%.

TABLE 2

| | Non-extruded Lyso-PS nanoparticles | | | |
| --- | --- | --- | --- | --- |
| | Unloaded Lyso-PS nanoparticles | FVIII-associated Lyso-PS nanoparticles | Insulin-associated Lyso-PS nanoparticles | Adalimumab-associated Lyso-PS nanoparticles |
| Size (nm) | 231.4 ± 30.1 | 245.5 ± 29.8 | 241.8 ± 14.4 | 302.2 |
| Chi-squared | 2.5 ± 4.6 | 2.8 ± 2.9 | 0.72 ± 0.6 | 2.8 |
| Zeta potential (mV) | −25.3 ± 3.3 | −19.0 ± 5.2 | | |
| Association efficiency (%) | — | 63.4% ± 5.3 | 84.8% ± 16.3 | 88.2% ± 9.4 |

TABLE 3

| | Non-extruded PS nanoparticles | | |
| --- | --- | --- | --- |
| | Unloaded PS nano-particles | FVIII-associated PS nano-particles | Insulin-associated PS nano-particles |
| Size (nm) | 1155.9 ± 95.0 | 1048.0 ± 192.9 | 676.9 ± 81.6 |
| Chi-squared | 175.0 ± 19.8 | 155.1 ± 34.6 | 100.5 ± 67.7 |
| Zeta potential (mV) | −31.2 ± 2.0 | −15.5 ± 1.3 | |
| Association efficiency (%) | — | 63.7% | 75.2% ± 4.9 |

Example 2

The following example provides a description of a method of making a liposome of the present disclosure.

PS containing particles were prepared at a 30:70 molar ratio of PS to DMPC using the dry film method as previously described. The film was then rehydrated in appropriate buffer (Tris buffer, 150 mM sodium chloride, 25 mM Tris, pH 7.0 for FVIII and OVA, or phosphate buffered saline (PBS), pH 5.5 for GAA) and extruded multiple times through a double-stacked polycarbonate membrane of pore size 200 nm using a high-pressure extruder. Final concentration of the nanoparticle preparations was confirmed via a standard phosphate assay. The particle size and polydispersity index was measured using light scattering measurements (Table 4). Particle sizes were determined by dynamic light scattering (DLS) using a Particle Sizer and Zeta Potential Analyzer (Brookhaven's NanoBrook Omni, Holtsville, NY). Samples were allowed to equilibrate for 60 seconds prior to each run. Measurements were performed at 25° C. with the duration of 100 seconds for a total of three measurements each run.

TABLE 4

| Particle size as a function of lipid composition. | | |
| --- | --- | --- |
| Lipid composition | Mean particle size ± SD (nm) | Polydispersity ± SD |
| DMPC (100%) | 189 ± 24.9 | 0.17 ± 0.02 |
| Brain PS (30%) | 169 ± 9.3 | 0.15 ± 0.03 |
| 18:1 PS (30%) | 169 ± 0.4 | 0.13 ± 0.03 |

TABLE 4-continued

| Particle size as a function of lipid composition. | | |
| --- | --- | --- |
| Lipid composition | Mean particle size ± SD (nm) | Polydispersity ± SD |
| 18:1 Lyso-PS (30%) | 112 ± 9.6[*†‡¥] | 0.10 ± 0.02 |
| 18:0 Lyso-PS (30%) | 175 ± 6.4 | 0.13 ± 0.01 |

[*]Significant difference from DMPC
[†]Significant difference from Brain PS
[‡]Significant difference from 18:1 PS
[¥]Significant from 18:0 lyso-PS Table 4 shows particle size and size distribution of nanoparticles containing different species of PS varying in degree of saturation and number of acyl chains after extrusion using 200 nm polycarbonate filter. One-way ANOVA followed by Tukey's post-hoc multiple comparison test were performed to detect significant differences ($P<0.05$).

Example 3

The following example provides a description of evaluating the exposure of a dye on the surface of a liposome of the present disclosure.

A titration study using PSvue 550 as the fluorescence probe was conducted to evaluate the exposure of PS on the surface of PS and Lyso-PS nanoparticles. The final concentration of PSvue was maintained at 1 μM while the concentration of all nanoparticle formulations was ranging from 0-280 μM. Immediately after the addition of PSvue into the formulations, samples were excited at 550 nm and emission intensity was measured at 610 nm using a SpectraMax i3 Multi-Mode Microplate Reader (Molecular Device, Sunnyvale, CA). Fluorescence intensity was normalized using the emission intensity of PSvue alone in the absence of any lipids. Changes in fluorescence intensity were plotted as a function of total lipid concentration and fitted in GraphPad Prism software using a single site-total binding model with nonlinear least squares fitting to evaluate for PS surface exposure (FIG. 1).

Example 4

The following example describes formation of a liposome of the present disclosure.

Method: Lyso-PS film (lyso-PS 18:1) was rehydrated in at pH 6, then incubated at 37° C. for 2 min followed by 15 sec vortexing. This process was repeated for a total of 3 cycles.

Association of the nanoparticles with AAV8 was conducted through the trigger-loading method at 37° C.

TABLE 5

| Particle size of liposomes loaded with AAV 8. | |
| --- | --- |
| Protein Rehydration | Size (nm) |
| Trial 1 | 211.9 |
| Trial 2 | 109.6 |
| Trial 3 | 226.1 |

TABLE 6

| Particle size of liposomes loaded with AAV 8 where the method of making further comprises an extrusion step. | |
| --- | --- |
| Trial number | Size (nm) |
| Trial 1 | 124.1 |
| Trial 2 | 106.9 |

The associate efficiency was about 43%.

Aquaporin 4 was trigger loaded in a Lyso-PS 18:1 liposomes in citrate buffer at pH 5 and 37° C.

Although the present disclosure has been described using specific embodiments and examples, routine modifications will be apparent to those skilled in the art and such modifications are intended to be within the scope of the disclosure and the claims.

The invention claimed is:

1. A method of preparing liposomes having an average diameter of less than 300 nm, wherein at least 95% of the particles have a diameter of 200-275 nm, comprising:

mixing a plurality of lipids comprising phosphatidylcholine (PC) and lysophosphatidylserine (lyso-PS), wherein the ratio of PC to lyso-PS is from 90:10 to 60:40, incubating the plurality of lipids for 30 seconds to 5 minutes, and vortexing the mixture, wherein the liposomes formed have an average diameter of less than 300 nm and 95% of the particles have a diameter of 200-275 nm, and wherein the method does not comprise an extrusion step.

2. The method of claim 1, wherein the ratio of PC to lyso-PS is from 85:15 to 70:30.

3. The method of claim 1, wherein the PC is present as dimyristoyl-sn-glycero-3 phosphatidylcholine (DMPC).

4. The method of claim 1, wherein PC and lyso-PS are the only phospholipids present in the bilayer of the liposomes.

5. The method of claim 1, wherein the lyso-PS is 18:1.

6. The method of claim 1, wherein the lyso-PS is L-lyso-PS.

7. The method of claim 1, wherein the vortexing is done from 30 seconds to 3 minutes.

8. The method of claim 1, further comprising trigger loading a protein into the liposome.

9. The method of claim 8, wherein the protein is loaded into a liposomal bilayer.

10. The method of claim 8, wherein the conformation of the protein is altered by heating the protein to about 37° C.

11. The method of claim 10, wherein the protein is chosen from AAV proteins, collagens, aquaporin 4, cas proteins, insulin, Factor VIII, Adalimumab, and alpha glucosidase (GAA).

12. The method of claim 1, wherein the mixing comprises contacting the plurality of lipids with a buffered aqueous solution.

13. The method of claim 12, wherein prior to the mixing, each lipid of the plurality of lipids are thin lipid films.

14. The method of claim 13, wherein the thin lipid films are formed from allowing a solution to dry, wherein the solution comprises an organic solvent and one or more lipids.

15. The method of claim 14, wherein the organic solvent is chosen from ethanol, methanol, and isopropyl ether.

* * * * *